(12) United States Patent
Hanlon et al.

(10) Patent No.: US 9,572,720 B2
(45) Date of Patent: Feb. 21, 2017

(54) REDUCED NOISE PNEUMATIC COMPRESSION GARMENT

(75) Inventors: James G. Hanlon, Morgan Hill, CA (US); David Rork Swisher, St. Charles, MO (US)

(73) Assignee: Covidien LP, Mansfield, MA (US)

( * ) Notice: Subject to any disclaimer, the term of this patent is extended or adjusted under 35 U.S.C. 154(b) by 2065 days.

(21) Appl. No.: 12/569,074

(22) Filed: Sep. 29, 2009

(65) Prior Publication Data

US 2011/0077565 A1 Mar. 31, 2011

(51) Int. Cl.
*A61F 5/00* (2006.01)
*A61F 13/08* (2006.01)

(52) U.S. Cl.
CPC .................................. *A61F 13/085* (2013.01)

(58) Field of Classification Search
CPC .. A61H 2205/12; A61H 9/005; A61H 9/0078; A61H 9/0092; A61H 2209/00; B01D 46/0005; B01D 46/0012; A61B 17/135; A61F 5/0111; A61F 5/34; A61F 5/12; A61F 13/06; A61F 13/085; A61F 5/012; A47L 9/0081; A61M 16/101; A61M 2205/42
USPC ...................... 601/148, 151, 152; 602/13, 23
See application file for complete search history.

(56) References Cited

U.S. PATENT DOCUMENTS

| | | |
|---|---|---|
| 3,677,300 A | 7/1972 | King |
| 3,736,074 A | 5/1973 | Kilbane et al. |
| 3,855,910 A | 12/1974 | Brinton et al. |
| 3,944,084 A | 3/1976 | Reeves |
| 3,946,735 A | 3/1976 | DeWall |
| 4,135,500 A | 1/1979 | Gorran |
| 4,264,282 A | 4/1981 | Crago |
| 4,399,739 A | 8/1983 | Dean |
| 4,418,443 A | 12/1983 | Fischer |
| 4,435,877 A | 3/1984 | Berfield |
| 4,450,933 A | 5/1984 | Fukuoka et al. |
| 4,534,343 A | 8/1985 | Nowacki et al. |
| 4,606,328 A | 8/1986 | Thoman |
| 4,729,722 A | 3/1988 | Toth |
| 4,872,448 A | 10/1989 | Johnson, Jr. |
| 4,888,003 A | 12/1989 | Johnson et al. |
| 4,911,697 A | 3/1990 | Kerwin |
| 4,921,477 A | 5/1990 | Davis |
| 4,991,617 A | 2/1991 | Butler |

(Continued)

FOREIGN PATENT DOCUMENTS

| | | |
|---|---|---|
| EP | 0897707 A2 | 2/1999 |
| GB | 2271060 A | 4/1994 |

(Continued)

OTHER PUBLICATIONS

Website, www.newenglandfoam.com/filter.html.*

*Primary Examiner* — Ophelia A Hawthorne
*Assistant Examiner* — Caitlin Carreiro

(57) ABSTRACT

A reduced noise pneumatic compression garment includes a flexible member having a bladder that can conform to a limb of the human body. A port in fluid communication with the bladder has an air flow path through which pressurized air is delivered to the bladder to inflate the bladder. A porous insert is located within the flow path of the port between the air inlet and the air outlet for reducing noise from air flow through the port into the inflatable chamber. A method of quietly inflating a pneumatic compression garment is also disclosed.

20 Claims, 17 Drawing Sheets

(56) References Cited

U.S. PATENT DOCUMENTS

| | | | |
|---|---|---|---|
| 5,047,072 A | 9/1991 | Wertz et al. | |
| 5,118,262 A | 6/1992 | Kuo | |
| 5,147,243 A | 9/1992 | Inglis et al. | |
| 5,174,127 A | 12/1992 | Harper et al. | |
| 5,214,253 A | 5/1993 | Houston, Jr. | |
| 5,220,811 A | 6/1993 | Harper et al. | |
| 5,260,524 A | 11/1993 | Schroeder et al. | |
| 5,285,791 A | 2/1994 | Smith | |
| 5,353,525 A * | 10/1994 | Grim | 36/88 |
| 5,354,260 A | 10/1994 | Cook | |
| 5,449,379 A | 9/1995 | Hadtke | |
| 5,599,333 A | 2/1997 | Atkinson | |
| 5,628,306 A | 5/1997 | Kee | |
| 5,804,777 A | 9/1998 | Kim et al. | |
| 5,858,062 A | 1/1999 | McCulloh et al. | |
| 5,961,309 A | 10/1999 | Harpole et al. | |
| 5,996,731 A | 12/1999 | Czabala et al. | |
| 6,089,346 A | 7/2000 | Tredinnick et al. | |
| 6,126,393 A | 10/2000 | Arnold | |
| 6,231,009 B1 | 5/2001 | Kong | |
| 6,280,153 B1 | 8/2001 | Iversen et al. | |
| 6,340,069 B1 | 1/2002 | Wang | |
| 6,382,931 B1 | 5/2002 | Czabala et al. | |
| 6,447,491 B1 | 9/2002 | Lord | |
| 6,558,137 B2 | 5/2003 | Tomell et al. | |
| 6,579,075 B2 | 6/2003 | Lee et al. | |
| 6,623,239 B2 | 9/2003 | Sahay et al. | |
| 6,663,596 B2 | 12/2003 | Griego et al. | |
| 6,702,880 B2 | 3/2004 | Roberts et al. | |
| 6,743,250 B2 | 6/2004 | Renfro | |
| 6,749,592 B2 | 6/2004 | Lord | |
| 6,840,746 B2 | 1/2005 | Marshall et al. | |
| 6,866,700 B2 | 3/2005 | Amann | |
| 6,935,460 B2 | 8/2005 | McCombs et al. | |
| 7,070,567 B2 | 7/2006 | Mizukoshi et al. | |
| 7,141,101 B2 | 11/2006 | Amann | |
| 7,153,107 B1 | 12/2006 | Maddox, Jr. | |
| 7,452,340 B2 | 11/2008 | Cook et al. | |
| 7,967,766 B2 | 6/2011 | Ravikumar | |
| 2002/0027041 A1 | 3/2002 | Czabala et al. | |
| 2002/0071765 A1 | 6/2002 | Sahay et al. | |
| 2002/0087131 A1 | 7/2002 | Wolff et al. | |
| 2002/0193761 A1 | 12/2002 | Lord | |
| 2003/0213368 A1 * | 11/2003 | Roberts et al. | 96/381 |
| 2003/0235507 A1 | 12/2003 | Kwang-Tsan | |
| 2004/0126247 A1 | 7/2004 | Broser et al. | |
| 2004/0241012 A1 | 12/2004 | Kim et al. | |
| 2004/0261621 A1 | 12/2004 | Lindsay | |
| 2005/0067218 A1 | 3/2005 | Bristow et al. | |
| 2005/0126204 A1 | 6/2005 | Piccirilli et al. | |
| 2005/0143682 A1 | 6/2005 | Cook et al. | |
| 2006/0111655 A1 | 5/2006 | Cook et al. | |
| 2006/0251527 A1 | 11/2006 | Wester | |
| 2007/0019047 A1 | 1/2007 | Kleinert et al. | |
| 2007/0135743 A1 * | 6/2007 | Meyer | 601/152 |
| 2007/0276313 A1 | 11/2007 | Moorehead et al. | |
| 2007/0290012 A1 | 12/2007 | Jackman | |
| 2008/0030747 A1 | 2/2008 | Shingai | |
| 2008/0082059 A1 | 4/2008 | Fink et al. | |
| 2008/0087169 A1 | 4/2008 | Clark | |
| 2008/0103422 A1 | 5/2008 | Perry et al. | |
| 2008/0200872 A1 | 8/2008 | Isham | |

FOREIGN PATENT DOCUMENTS

| | | |
|---|---|---|
| GB | 0217996.8 | 8/2002 |
| WO | 2004012644 A1 | 2/2004 |
| WO | 2005063164 A1 | 7/2005 |

* cited by examiner

FIG. 16

| Controller | Port | Foam | Mean Peak Flow Rate (LPM) | Mean Rise Time to Peak Pressure (Seconds) | Mean Maximum Noise (dB) |
|---|---|---|---|---|---|
| 1 | Standard | N/A | 72.068 | 0.135 | 78.60 |
| | E2 | 10 ppi | 71.399 | 0.138 | 66.26 |
| | E2 | 20 ppi | 69.659 | 0.147 | 66.76 |
| | E1 | 10 ppi | 74.130 | 0.139 | 67.02 |
| | E1 | 20 ppi | 72.830 | 0.144 | 66.78 |
| 2 | Standard | N/A | 69.683 | 0.137 | 77.20 |
| | E2 | 10 ppi | 68.640 | 0.141 | 67.92 |
| | E2 | 20 ppi | 67.622 | 0.144 | 67.46 |
| | E1 | 10 ppi | 70.810 | 0.142 | 68.08 |
| | E1 | 20 ppi | 69.590 | 0.146 | 65.10 |

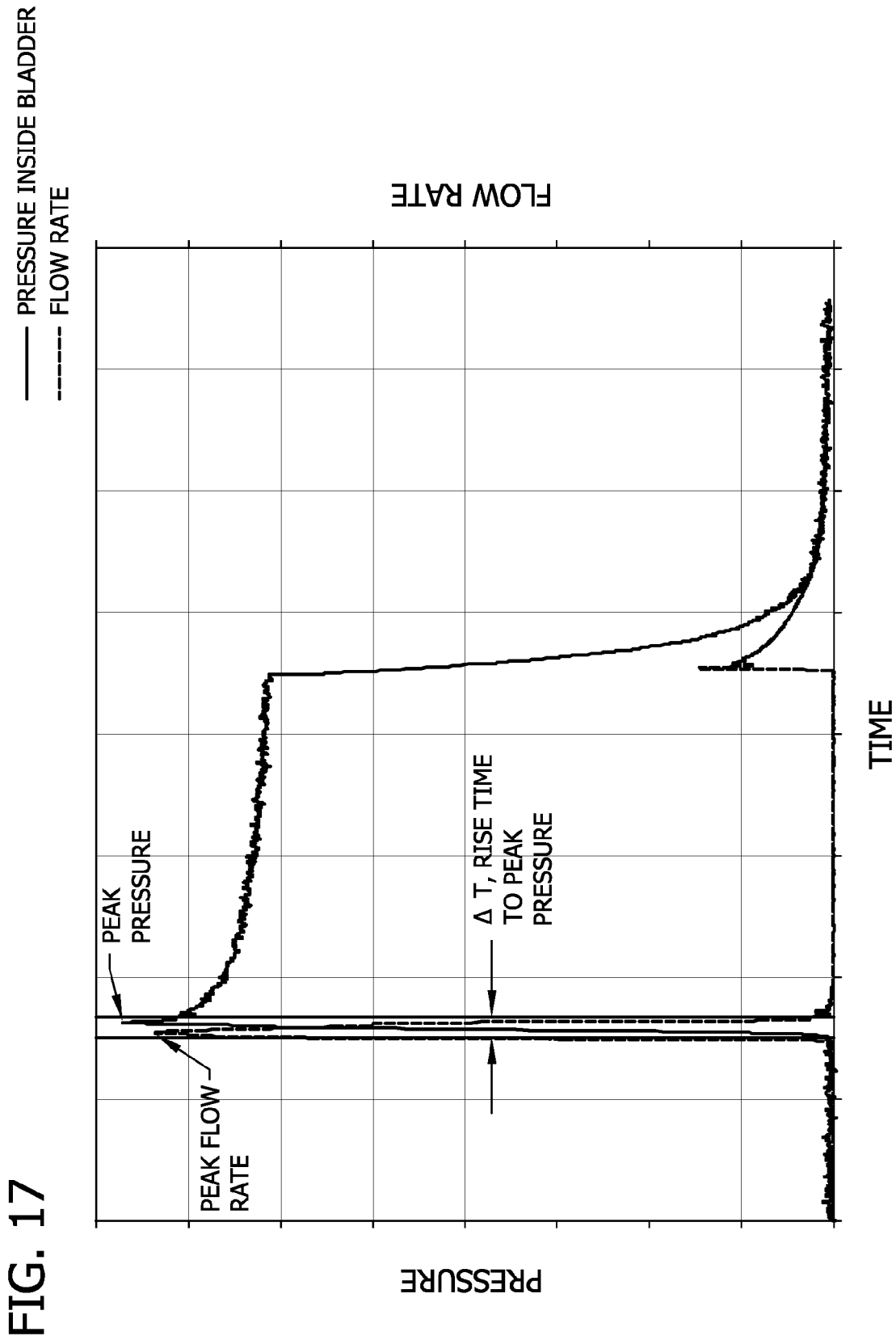

REDUCED NOISE PNEUMATIC COMPRESSION GARMENT

FIELD OF THE INVENTION

The present disclosure generally relates to a compression garment configured for applying compressive forces to a portion of a wearer's body. In particular, the present disclosure relates to a porous insert located within a flow path of a port for attenuating noise generated from air flow into an inflatable chamber of the compression garment.

BACKGROUND OF THE INVENTION

Compression garments for applying compressive forces to a selected area of a wearer's body are generally employed to improve blood flow in the selected area. Compression garments in which intermittent pulses of compressed air are delivered to at least one inflatable chamber in a cuff or sleeve of the garment are particularly useful. This cyclic application of pressure provides a non-invasive method of prophylaxis to reduce the incidence of deep vein thrombosis (DVT) and improve blood flow.

In general, a compression garment of the type described above includes a flexible member having an inflatable bladder disposed therein. The compression garment is placed around the patient's foot or other selected limb, and a pressurized fluid or air is delivered rapidly into the inflatable bladder to create pressure at the part or parts of the body in contact with the bladder. The air is then evacuated and the cycle is repeated. The high velocity or flow rate of the pressurized fluid/air entering the bladder produces noise that can be unpleasant to the wearer of the compression device.

SUMMARY OF THE INVENTION

One aspect of the present invention is directed to a reduced noise pneumatic compression garment comprising a flexible member adapted to conform to at least a portion of a limb of a human body and to retain itself on the limb. A bladder associated with the flexible member conformable to at least a portion of the limb defines an inflatable chamber. The bladder has an opening through which the inflatable chamber is inflated. A port mounted on the bladder has an air inlet, an air outlet, and an air flow path between the air inlet and air outlet. The air inlet is adapted for communication with a source of pressurized air, and the air outlet is in communication with the inflatable chamber via the opening in the bladder. Delivery of air from the source of pressurized air into the inflatable chamber through the air flow path inflates the inflatable chamber and thereby applies a compression force to the limb when the flexible member is on the limb. A porous insert located within the flow path of the port between the air inlet and the air outlet reduces noise from air flow through the port into the inflatable chamber.

In another aspect of the invention, a method of quietly inflating a pneumatic compression garment comprises delivering a flow of pressurized gas through a port to an inflatable chamber of a flexible member adapted to be received on a human body to compress the body. The method further comprises changing a direction of flow of the pressurized gas between an inlet of the port and an outlet of the port. In addition, the method comprises diffusing the flow of pressurized gas to the inflatable chamber through labyrinthine passages within the port and passing the diffused flow into the inflatable chamber.

Other objects and features will be in part apparent and in part pointed out hereinafter.

BRIEF DESCRIPTION OF THE DRAWINGS

FIG. 16 is a table showing test results comparing performance criteria of a standard compression garment with compression garments constructed according to the principles of the present invention; and FIG. 17 is an example graph of data collected during testing.

Corresponding reference characters indicate corresponding parts throughout the drawings.

DETAILED DESCRIPTION

Figure 1:
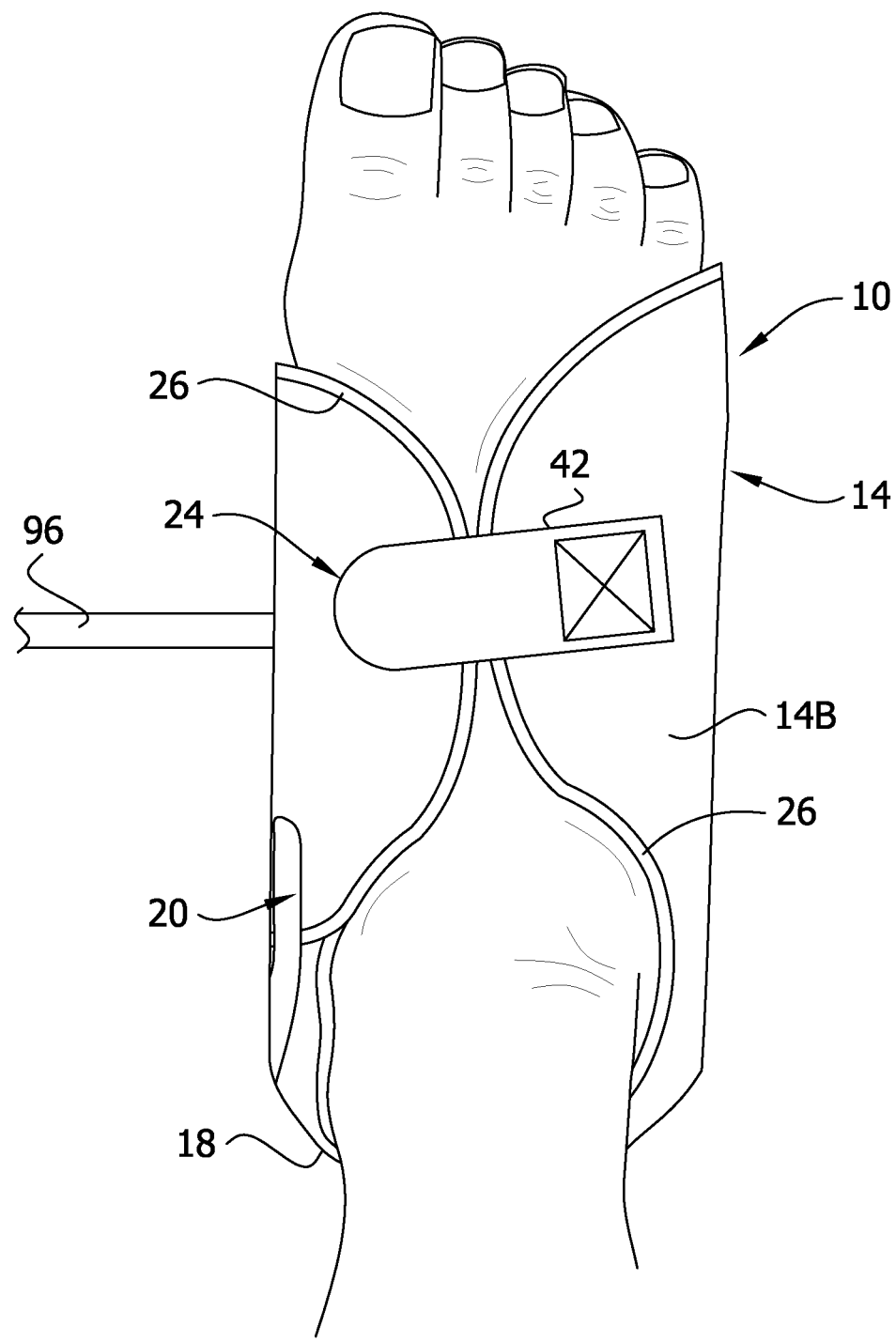
FIG. 1 is a top view of a compression garment as applied to a foot of a patient.
Figure 2:
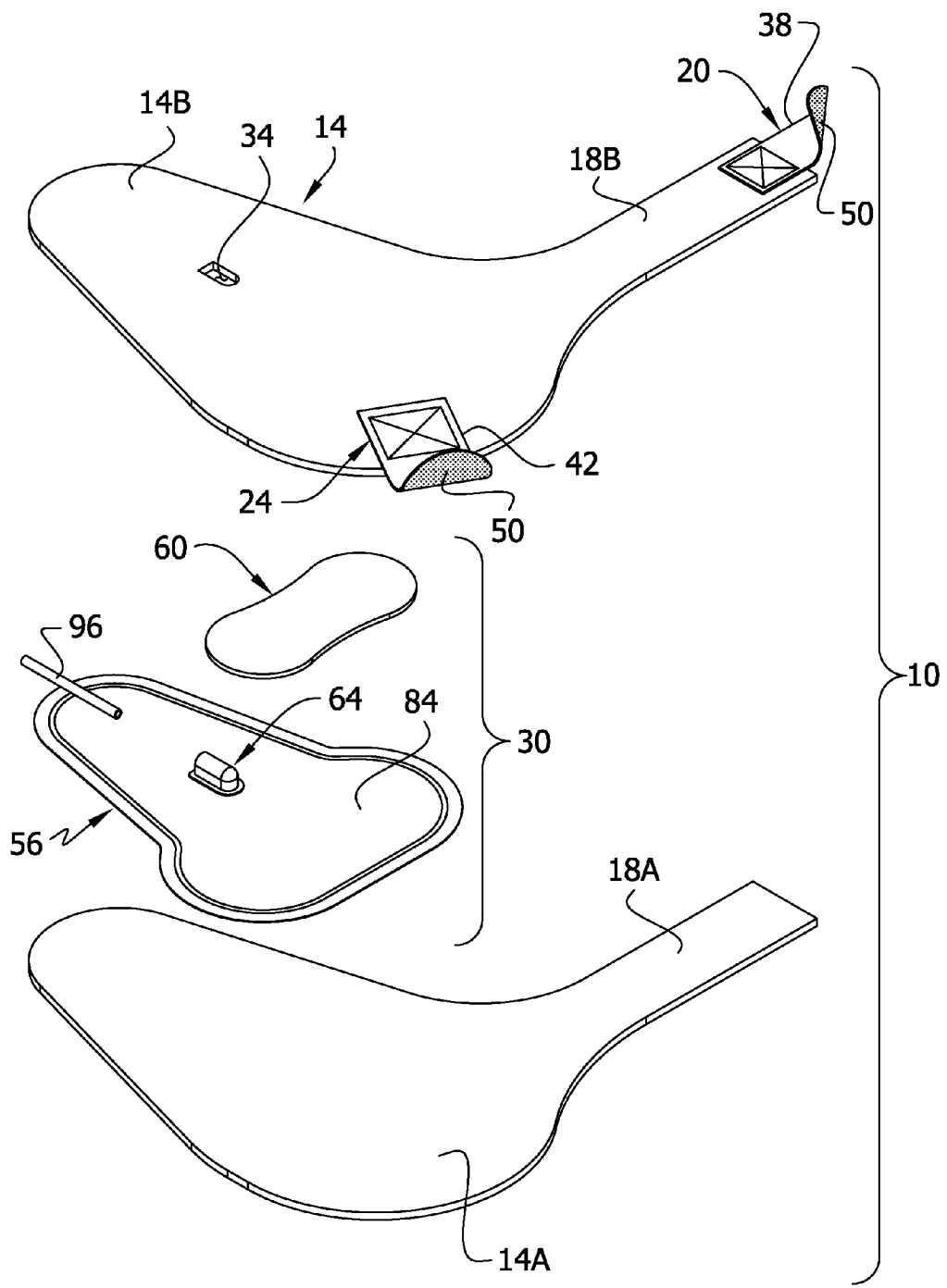
FIG. 2 is an exploded perspective of the compression garment of FIG. 1.

With reference to FIGS. 1 and 2, a first embodiment of a compression garment in accordance with the present disclosure is illustrated as a foot cuff and is designated generally as 10. The foot cuff 10 is adapted for use in a compression therapy system for applying compressive pressure to a foot of a wearer, as is generally known in the art and will not be described herein.

In general, the foot cuff 10 comprises a flexible member 14 is adapted to conform to the foot and to retain itself on the foot. The member 14 includes an ankle strap 18 and is secured in a self-retaining configuration on the foot by two releasable fasteners 20, 24, which are described in more detail below. It is understood that the foot cuff 10 may have other configurations within the scope of the present invention. It is also understood that compression garments other than foot cuffs are within the scope of the present invention, including but not limited to leg compression sleeves, arm compression sleeves, and similar devices. Moreover, although the present invention has particular application to garments that are cyclically inflated and deflated, it could be used in garments having different uses, such as for treating edema, wound healing, etc.

The flexible member 14 comprises an inner (contact) layer 14A and an outer layer 14B secured to one another along a seam 26 generally adjacent corresponding perimeters of the layers to define an interior space for receiving and substantially enclosing a bladder assembly, generally designated 30. The inner and outer layers 14A, 14B may be fixedly secured to one another, such as by heat welding, adhesives, sewing, or other suitable ways. Alternatively, the layers 14A and 14B may be releasably secured to one another. In use, the inner layer 14A is adjacent to the wearer's foot and the outer layer 14B is located farthest from the foot. As used herein, the terms "inner" and "outer" indicate relative positions of respective components and surfaces with respect to the skin of the wearer's body part when the compression garment is secured to the body part, and as such, an "inner" component or surface is more adjacent to the skin of the body part than an "outer" component or surface.

The inner layer 14A and the outer layer 14B of the flexible member 14 include ankle strap portions 18A and 18B respectively. The ankle strap portions 18A, 18B are elongate for wrapping about a portion of the foot adjacent to the ankle. The ankle strap portions 18A, 18B can be sewn, RF welded, or sonic welded to respective inner and outer layers 14A, 14B. However, in the illustrated embodiment, the ankle strap portions 18A, 18B are formed as one piece with the inner layer 14A and the outer layer 14B, respectively.

The inner layer 14A of the flexible member 14 is adapted for contacting the foot. In one embodiment, this layer 14A is fabricated from a chemically treated material, with wicking ability, for wicking moisture away from the skin. Furthermore, the inner layer 14A can be faced with a soft material toward the treatment surface of the wearer. For example, the soft material can be a thin layer of open celled porous foam, napped cloth, or a layer of vapor permeable cloth. It is understood that flexible members 14 not including an inner layer 14A or an outer layer 14B are within the scope of the present invention. Structure used to secure a bladder on a limb and maintain a position of the bladder can be a "flexible member."

Again referring to FIGS. 1 and 2, the outer layer 14B of the flexible member 14 includes an opening 34 for allowing passage of pressurized air to the bladder assembly 30. The outer layer 14B is configured for providing an attachment surface for a hook and loop feature of the foot cuff 10, as will be described in more detail below. Moreover, the outer layer 14B comprises a soft material for cushioning the top portion of the foot and may be fabricated from similar materials as the inner layer 14A and in similar dimensions therewith for corresponding geometry. Alternatively, the outer layer 14B may be fabricated from a laminated material, such as, for example, open cell urethane foam, or loop fabric.

The releasable fasteners 20, 24 are positioned on and attached to the outer layer 14B of the foot cuff for securing the foot cuff 10 around the foot. The first fastener 20 comprises a tab 38 attached to the ankle strap portion 18B of the outer layer 14B of the foot cuff 10, and the second fastener 24 comprises a tab 42 attached to a surface of the outer layer 14B. Both tabs 38, 42 have hook elements 50. In use, when the ankle strap 18 is wrapped about the back of the foot, the hook elements 50 on the tabs engage loop elements (not shown) on the outer layer 14B of the foot cuff 10 to secure the cuff on the foot, as will be understood by those skilled in the field familiar with foot cuffs. The releasable fasteners 20, 24 may have portions (not shown) without fastening material thereon to provide convenient gripping locations on the hook fasteners so that the practitioner can readily separate the hooks 50 from the outer layer 14B. Other fastening structure may be used without departing from the scope of the present invention.

Figure 3:
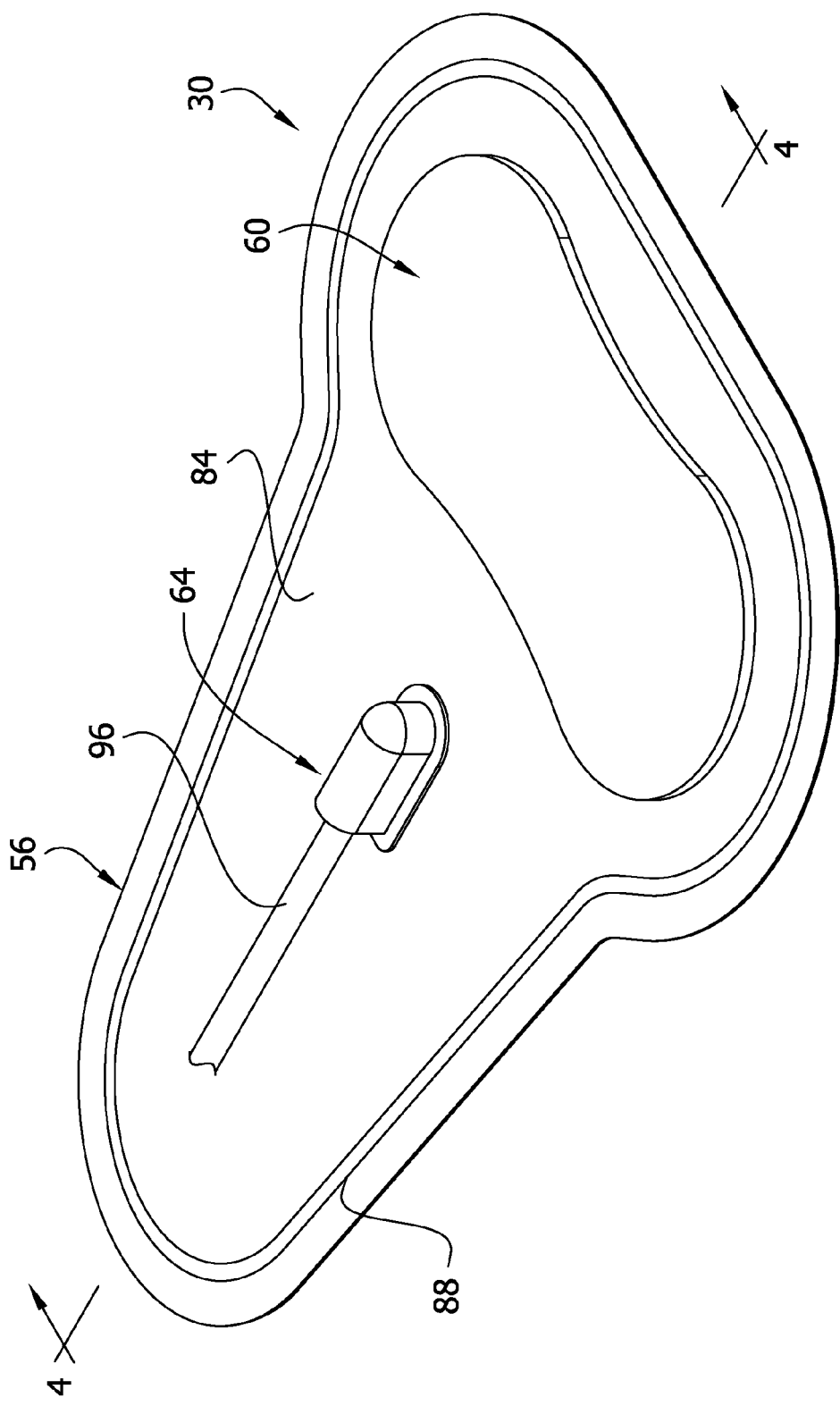
FIG. 3 is a bottom perspective of a first embodiment of a bladder assembly of the compression garment.
Figure 4:
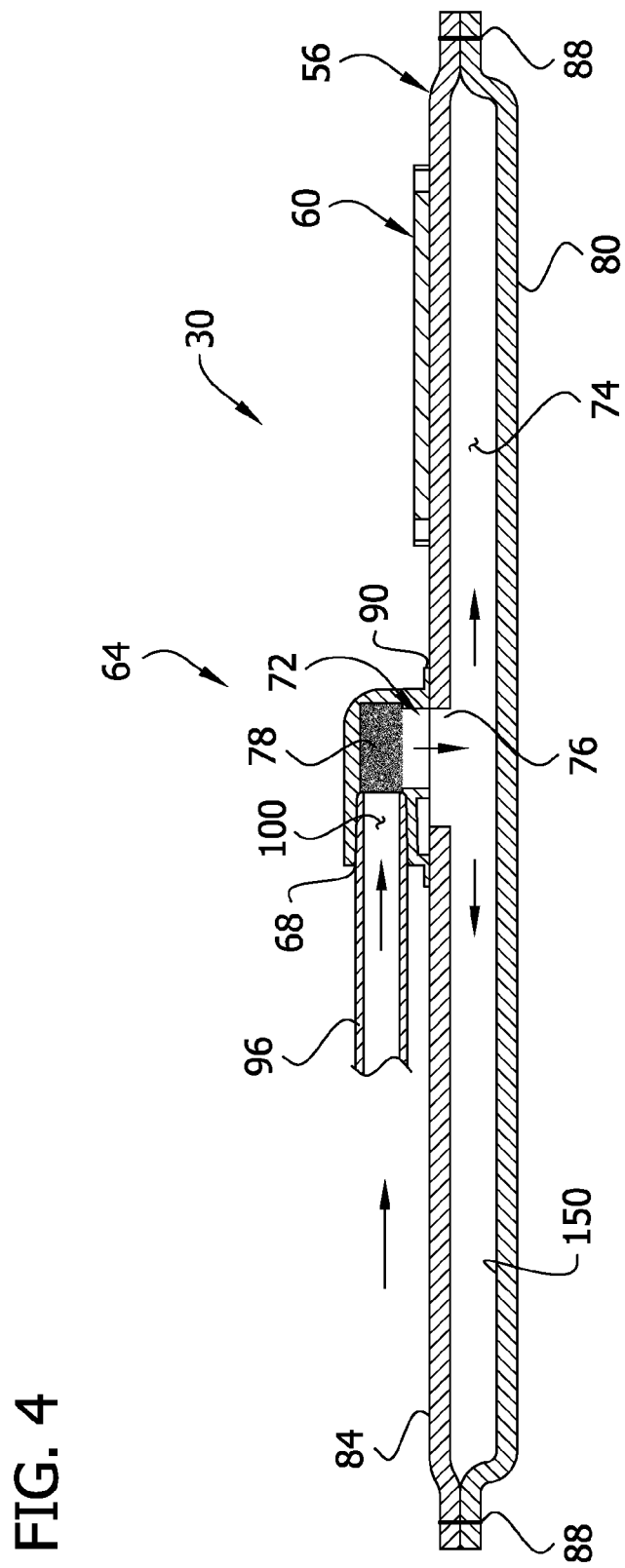
FIG. 4 is a section of the bladder assembly taken in the plane including line 4-4 in FIG. 3 and illustrating air flow into the bladder assembly.

Referring to FIGS. 2-4, the bladder assembly 30 is enveloped and enclosed by the flexible member 14. The assembly 30 comprises an inflatable bladder 56, a substantially rigid sole 60, and a port 64 having an air inlet 68 and air outlet 72. The bladder 56 defines an inflatable chamber 74 and has an opening 76 through which the inflatable chamber is inflated. The port 64 is mounted on the bladder 56 and is adapted for communication with a source of pressurized air (not shown). The air outlet 72 of the port 64 is in fluid communication with the inflatable chamber 74 via the opening 76 in the bladder 56 for delivery of air from the source of pressurized air into the inflatable chamber. As described in further detail below, a porous insert 78 is provided inside the port for reducing noise from air flow through the port into the inflatable chamber 74. Inflation of the inflatable chamber 74 applies a compression force to a foot of a wearer.

Still referring to FIGS. 2-4, the bladder 56 includes inner and outer opposing sheets 80, 84 of flexible air-impermeable material (e.g., PVC) joined together in a suitable manner along a seam 88 adjacent to their peripheries to define the inflatable chamber 74 (FIG. 4). As best illustrated in FIG. 2, the bladder 56 is positioned on the flexible member 14 such that the inflatable chamber 74 underlies the sole of the foot when the foot cuff 10 is placed on the foot. The inflatable chamber 74 is adapted for receiving and retaining pressurized air for exerting compressive pressure on the foot during successive pressure application cycles, as will be understood by those skilled in this field. The opposing sheets 80, 84 of the bladder 56 are joined to one another in a suitable manner, such as by RF welding. Other ways of joining the sheets 80, 84 include sewing, adhesive, heat sealing, etc. It is understood that the bladder 56 can have other configurations within the scope of this invention. For example, the bladder may be formed from one or more sheets and/or may include more than one inflatable chamber.

The sole 60 of the bladder assembly 30 is a substantially rigid member positioned between the outer sheet 84 of the bladder 56 and the outer layer 14B of the flexible member 14, and it extends generally lengthwise of the bottom of the foot when the foot cuff 10 is worn. The sole 60 provides a substantially rigid foundation against which the bladder 56 reacts during expansion. As a result, the expansion of the bladder 56 is directed toward the inner layer 14A of the flexible member 14 and the user's foot. The sole 60 is secured by suitable structure to maintain it in proper position relative to the bladder 56. It will be understood that the sole 60 may be omitted without departing from the scope of the present invention.

As shown in FIG. 4, the port 64 is positioned on the bladder 56 so that the bladder opening 76 lies within the port outlet 72 for delivery of air into the inflatable chamber 74. In one embodiment, the port 64 may have an overall length of approximately 1.28 in. (3.25 cm) and an overall width of approximately 0.69 in. (1.75 cm). A flange 90 is provided on the port 64 for securing the port to the bladder 56. The flange 90 is attached to the outer sheet 84 of the bladder 56 by suitable means, such as heat sealing, RF welding, or adhesive, for example. A tube 96 is connected to the air inlet 68 of the port 64 for delivery of air from the source of pressurized air (e.g., an air compressor) to the port. A suitable tube 96 may have an outside diameter of approximately 0.29 in. (0.74 cm) and an inside diameter of approximately 0.17 in. (0.43 cm). The port 64 comprises a flow path 100 extending through the port to permit flow of air from the port inlet 68 to the port outlet 72. In the illustrated embodiment, the port 64 forms and angle, and the flow path 100 changes direction approximately 90 degrees. The porous insert 78 is located within the flow path 100, between the air inlet 68 and the air outlet 72.

Figure 5:
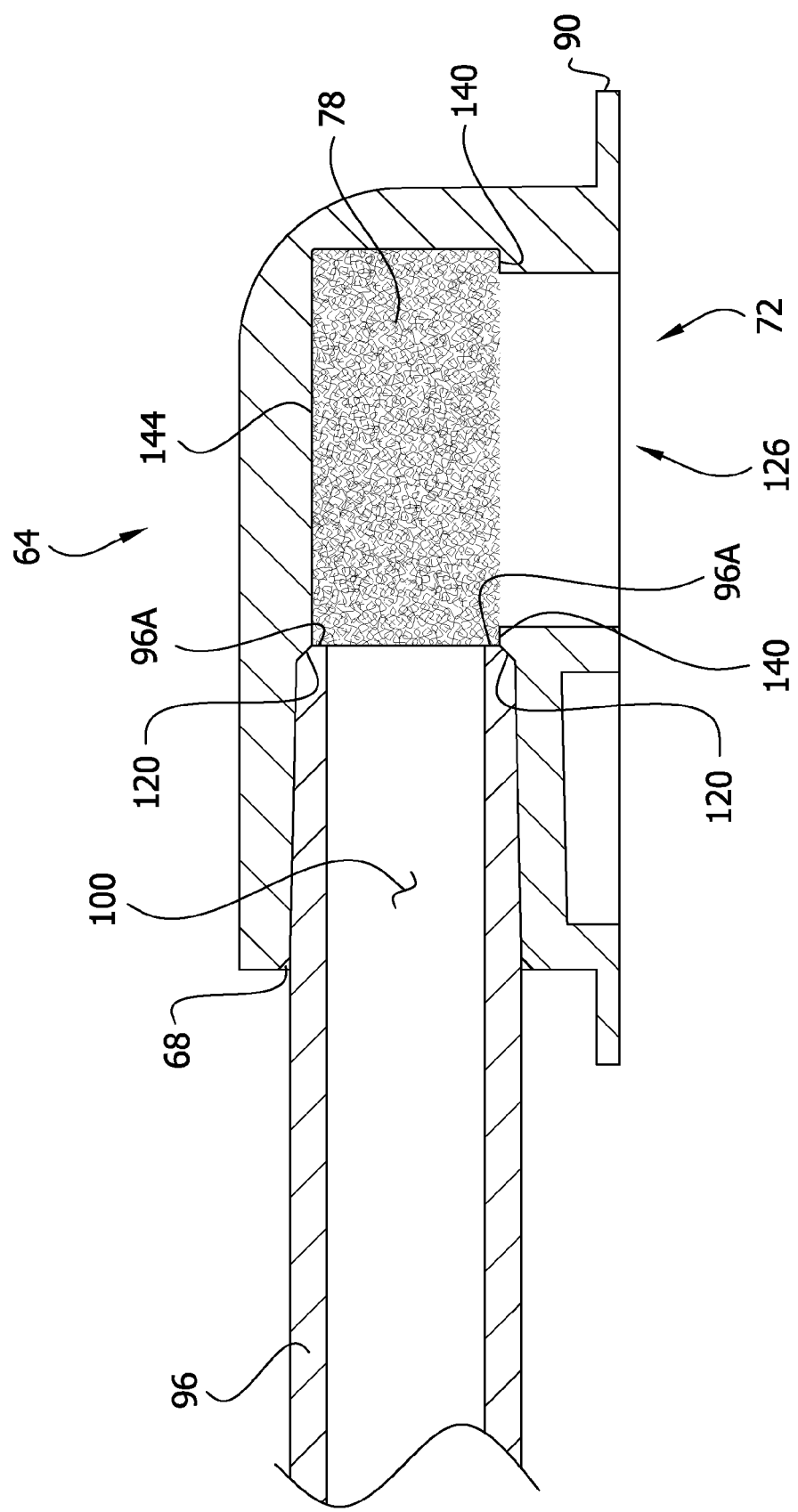
FIG. 5 is an enlarged section of a tube, port and porous insert of the bladder assembly.
Figure 8:
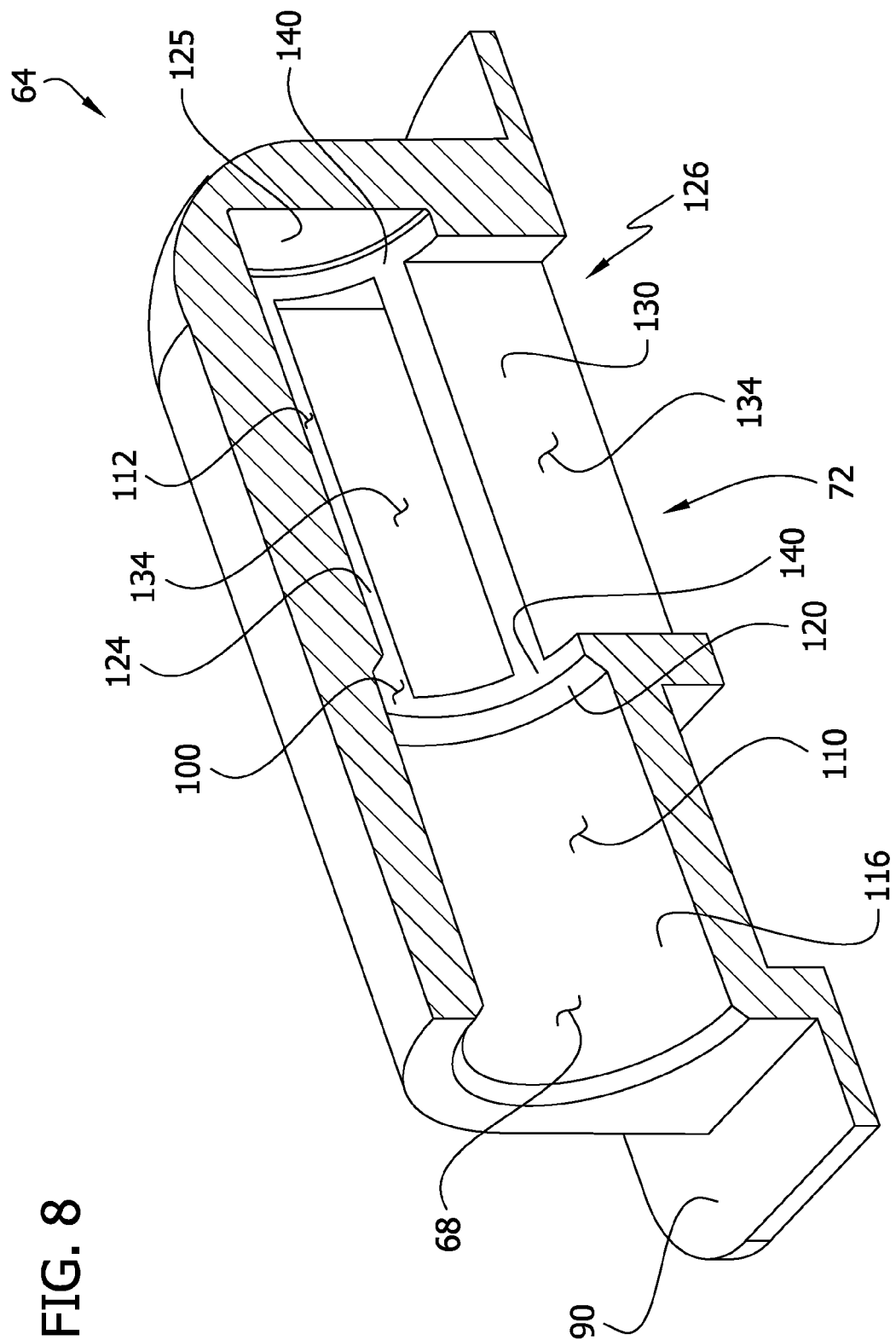
FIG. 8 is a section of the port taken in the plane including line 8-8 in FIG. 7.

Referring to FIG. 8, the flow path 100 of the port 64 comprises first and second chambers 110, 112. The first chamber 110 is adapted for receiving the tube 96. The chamber 110 is generally cylindrical and is defined by a side wall 116. The side wall 116 is tapered slightly from the port inlet 68 toward the second chamber 112. The average diameter of the chamber 110 is approximately the same as the outside diameter of the tube 96 (e.g., approximately 0.29 in. (0.74 cm)). As shown in FIG. 5, when the tube 96 is installed in the first chamber 110, an end 96A of the tube abuts against a circumferential shoulder 120 extending radially inward from the sidewall 116 of the first chamber 110 and essentially dividing the first chamber 110 from the second chamber 112. Movement of the tube 96 into the port 64 is limited by the shoulder 120. The tube 96 is sealed to the port 64 in a suitable manner, such as by solvent, heat sealing, RF welding, or adhesive, for example.

Figure 6:
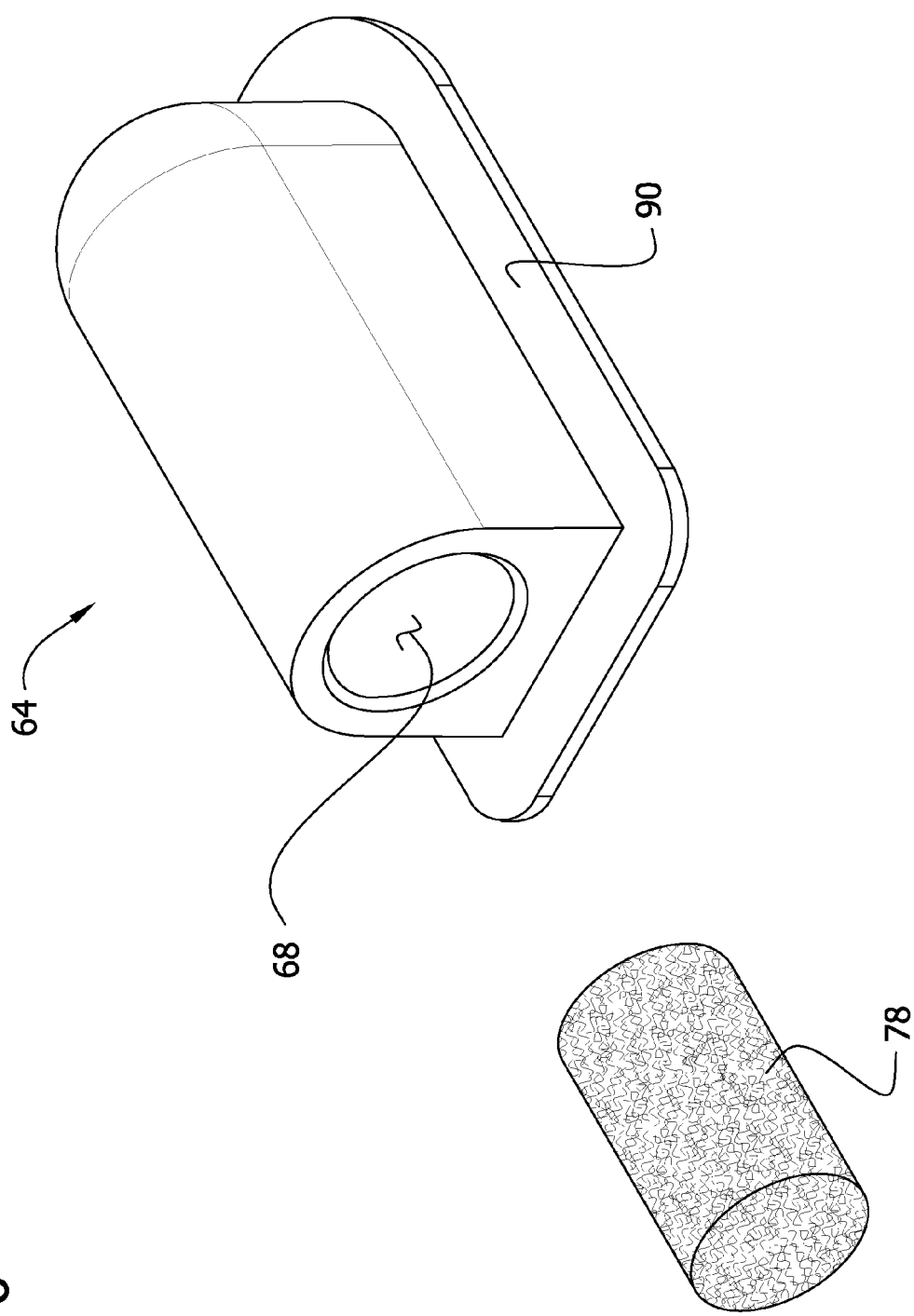
FIG. 6 is an enlarged bottom perspective of a port and porous insert of the bladder assembly.

Referring again to FIG. 8, the second chamber 112 is adapted for holding the porous insert 78, which is described in more detail below. The chamber 112 is generally cylindrical and is defined by a side wall 124 and an end wall 125. The diameter of the second chamber 112 (e.g., approximately 0.25 in. (0.64 cm)) is less than the diameter of the first chamber 110. The second chamber 112 is desirably shaped to generally correspond to the shape of the porous insert 78, and the second chamber is generally sized approximately the same as or smaller than the porous insert for reasons which will become apparent. In manufacture, the porous insert 78 is installed in the second chamber 112 through the first chamber 110, as illustrated in FIG. 6, and the tube 96 is then installed and sealed in the first chamber 110. As shown in FIG. 5, a circumferential edge margin of the tube end 96A extends radially inward from the shoulder 120 and contacts the porous insert 78. This prevents the porous insert 78 from moving from the second chamber 112 into the first chamber 110. It will be appreciated that dimensions and angles specified herein are examples only and do not limit the scope of the invention.

Figure 7:
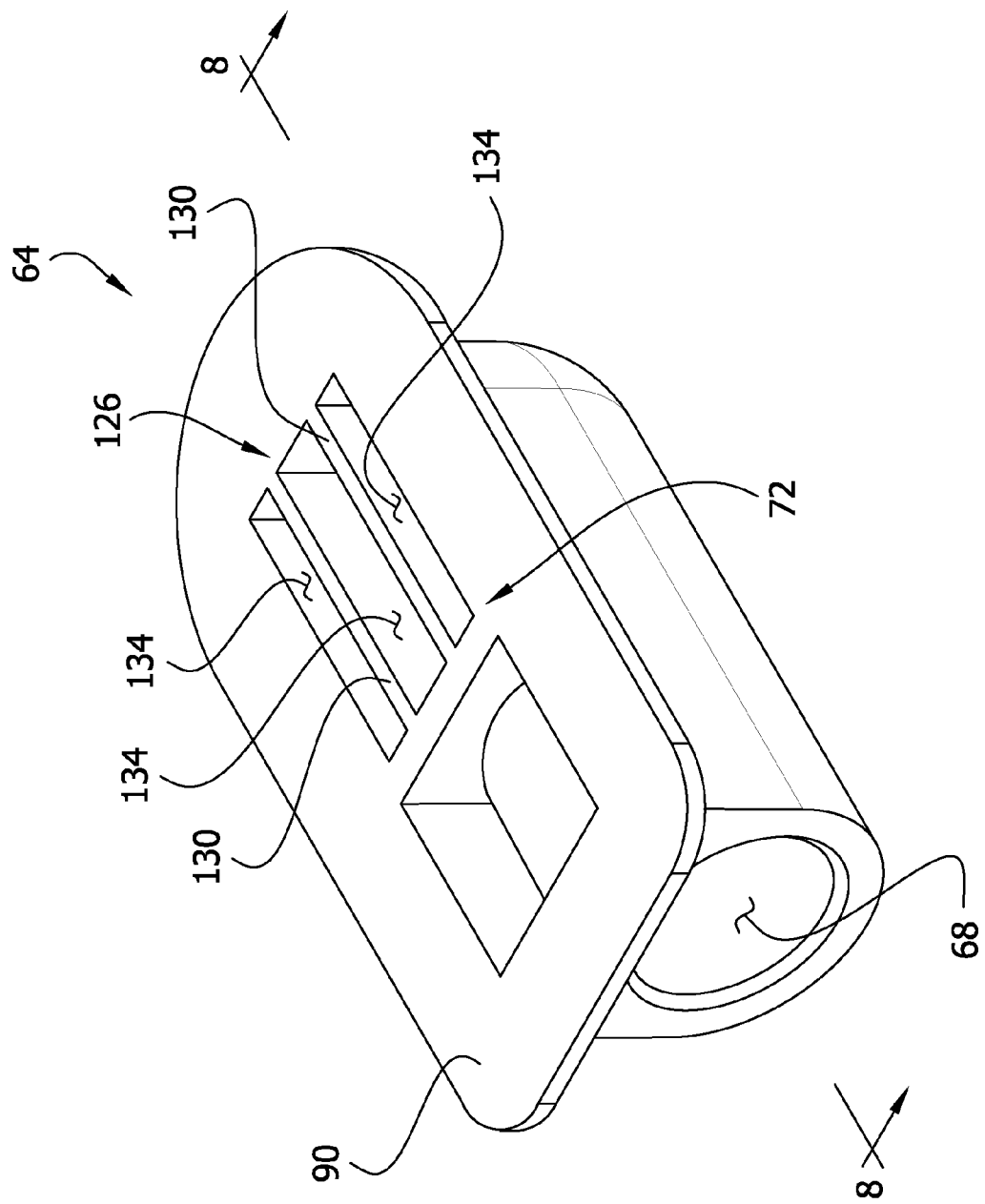
FIG. 7 is an enlarged top perspective of the port.

Referring to FIGS. 7 and 8, a retainer 126 is provided across the port outlet 72 for retaining the porous insert 78 within the second chamber 112 when air is delivered through the port 64 into the inflatable chamber 74. In the illustrated embodiment, the retainer 126 comprises two ribs 130 extending across the outlet 72 longitudinally of the port 64. In the illustrated embodiment, the ribs 130 are formed as one piece with the port 64 (e.g., by a molding operation) and divide the air outlet 72 into three separate rectangular openings 134. Inner ends of the ribs 130 comprise portions of the side wall 124 of the second chamber 112. As shown in FIGS. 5 and 8, cylindrical segments 140 comprise portions of the side wall 124 of the second chamber 112 at opposite ends of the ribs 130 that are not aligned with the outlet 72, as viewed in FIG. 5. The side wall portions 140 receive and retain the porous insert 78 within the second chamber 112. As shown in FIG. 5, the retainer 126 may also comprise an adhesive 144 between an interior surface (e.g., the side wall 124 of the second chamber 112) and the porous insert 78.

Other configurations of the port 64 are within the scope of the present invention. For example, the port 64 my have a different shape, which may include, for example, a flared port outlet in which the flow area through the port outlet 72 may be significantly larger than the flow area through the port inlet 68 and/or the flow area of the tube 96. Such an embodiment may allow for variation in the porosity (e.g., less porous) or other properties of the porous insert, as discussed in more detail below. In some embodiments, the flow path 100 may not change directions, or the flow path may change direction more than or less than 90 degrees. The port 64 may comprise more or fewer chambers 110, 112, and the chambers may be sized and/or shaped differently than illustrated. A retainer 126 having a different configuration is also within the scope of the present invention. For example, more or fewer ribs 130 may be used to form more or fewer outlet openings 134. In addition, the ribs 130 may have different shapes and sizes or be spaced further apart such that the openings 134 have different shapes and/or sizes.

The porous insert 78 is provided in the port 64 to reduce noise generated during inflation of the bladder 56. Noise may be generated in several ways during inflation of the bladder 56. Three potential sources of noise include "nozzle noise," "free jet noise," and "impingement noise." A large amount of turbulence is generated by friction between the pressurized air and the tube 96 as the pressurized air moves at a high velocity down the tube. Additional turbulence is generated in port geometries in which air flow is re-directed, such as the angled geometry of the illustrated port 64. This turbulence generates noise. The noise emanates from the port 64 in the form of "nozzle noise." When the pressurized air exits the port outlet 72, "free jet noise" is generated. "Impingement noise" may be generated when the pressurized air impinges against an impingement surface 150 inside the bladder 56. As shown in FIG. 4, the impingement surface 150 in the illustrated embodiment comprises the inner surface of the inner bladder sheet 80 facing the inflatable chamber 74 and opposing the air outlet 72 of the port 64. The porous insert 78 reduces the noise generated during inflation of the bladder 56 because the insert makes the flow of turbulent pressurized air more laminar before it exits the port 64. The porous insert 78 absorbs energy from the flow of turbulent pressurized air as it passes through the porous insert. In addition, the insert 78 causes the pressurized air to expand more quickly as it enters the bladder 56 and reduces noise generated by pressurized air impinging against the impingement surface 150.

As best shown in FIGS. 5 and 6, the porous insert 78 defines a multiplicity of labyrinthine internal passages arranged to provide fluid communication through the porous insert. For example, the porous insert 78 may comprise a fully reticulated or open cell polyurethane foam, a plastic-based matrix, a nonwoven mesh or a screen. The porous insert 78 may be flexible, semi-rigid or rigid. Several materials may be used, and suitable porosities may vary by material. For example, the porous insert 78 may comprise flexible reticulated or semi-reticulated foam having an uncompressed porosity between approximately 100 ppi and 5 ppi (254 ppc and 12.7 ppc); more desirably 60 ppi and 5 ppi (152.4 ppc and 12.7 ppc); and even more desirably 40 ppi and 10 ppi (101.6 ppc and 25.4 ppc). One such suitable foam may be obtained from Fritz Nauer A G, Oberwolfhauserstrasse, 8633 Wolfhausen, Switzerland, under the product name HDH 35 ANTH, product number 100017. As another example, the porous insert 78 may comprise a rigid plastic-based matrix having a porosity between 500 µM and 125 µM. One such suitable matrix may be obtained from Porex Technologies, 500 Bohannon Road, Fairburn, Ga. 30213, under the product number X-4912. Other suitable materials and porosities may be used.

The porous insert 78 may have any suitable shape. The illustrated insert 78 is cylindrical to correspond to the shape of the second chamber 112 of the port 64. However, the insert 78 may have a shape (e.g., rectangular) that does not correspond to the shape of the port 64. In addition, the insert 78 may be installed in the port 64 in alternative orientations, such as in a folded condition. Moreover, the insert 78 may have discontinuities such one or more bores through the insert or one or more ridges (e.g., radial wedge cuts) (not shown).

The porous insert 78 may have any suitable size. The insert 78 may be sized smaller than or approximately the same size as the second chamber 112 of the port 64. Alternatively, the insert 78 may be sized larger than the second chamber 112. For example, the porous insert 78 may be compressible and have a diameter and/or length larger than the second chamber 112. Thus, when installed in the second chamber 112, the porous insert 78 is compressed longitudinally and/or transversely. The porosity of the porous insert 78 may be changed according to the degree the insert is compressed within the port 64. For example, a piece of foam having a porosity of 10 ppi (25.4 ppc) may be sized (e.g., having a diameter of approximately 0.32 in. (0.81 cm)) such that when compressed in the port 64 the foam has an effective porosity of approximately 20 ppi (50.8 ppc). A piece of foam having a porosity of 20 ppi (50.8 ppc) may be sized such that when compressed in the port 64 the foam has an effective porosity of approximately 40 ppi (101.6 ppc). To accomplish such changes in porosity, the compression may reduce the volume of the porous insert 78 between approximately 5 percent and 90 percent, more preferably 10 percent and 80 percent, and even more preferably 40 percent and 70 percent. Compression may be desirable to increase the holding force between the porous insert 78 and inside surfaces of the port 64 to assist in retaining the insert within the port.

The port outlet 72 may have a flow area sized larger than a flow area of the port inlet 68 or the tube 96 (whichever is controlling). In the configuration illustrated in FIGS. 4-8, the flow area of the tube 96 is controlling (e.g., approximately 0.02 in.$^2$ (0.13 cm$^2$)), and the port outlet 72 has a flow area (e.g., approximately 0.10 in.$^2$ (0.65 cm$^2$)) sized approximately 5 times the flow area of the tube. The increased flow area of the port outlet 72 allows for increased flow of air out of the port 64 to account for reduced flow rate resulting from air pressure drop across the porous insert 78. The porous insert 78 desirably has a construction and porosity that causes minimal drop of pressure across the insert so that bladder pressures may be achieved sufficiently rapidly to effectuate desired blood flow characteristics in the patient. However, some pressure drop can occur as a result of the interference of the insert 78 with the flow of air through the port 64. The flow area of the port outlet 72 may have different sizes, ranging for example between approximately 2 and 8 times the flow area of the tube 96. Porous inserts that cause a moderate or significant drop of air pressure across the insert are within the scope of the present invention, as well as ports with outlets having a flow area sized the same as or smaller than the flow area of a port inlet or tube.

Figure 9:
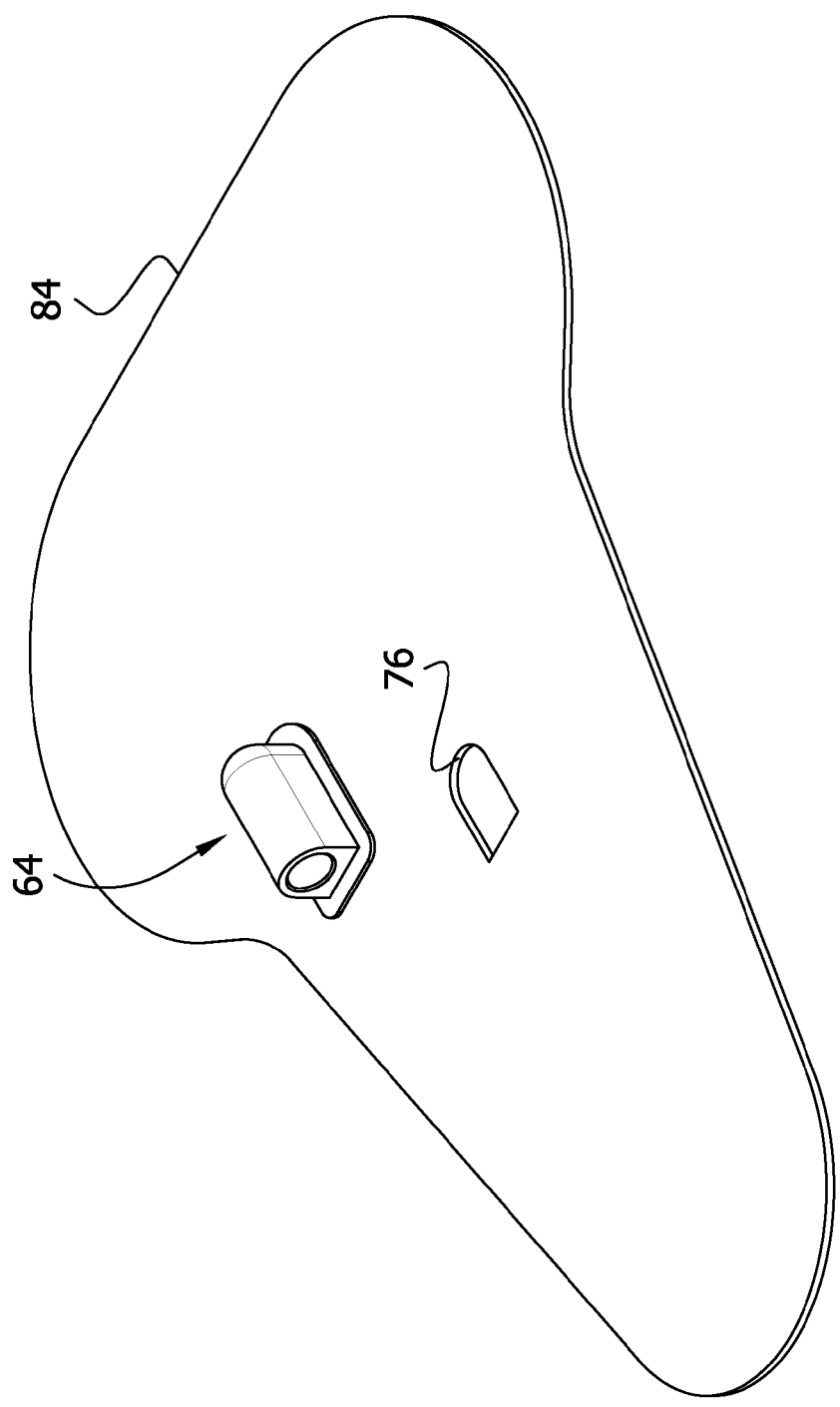
FIG. 9 is an exploded bottom perspective of the port and a bladder sheet of the bladder assembly.
Figure 10:
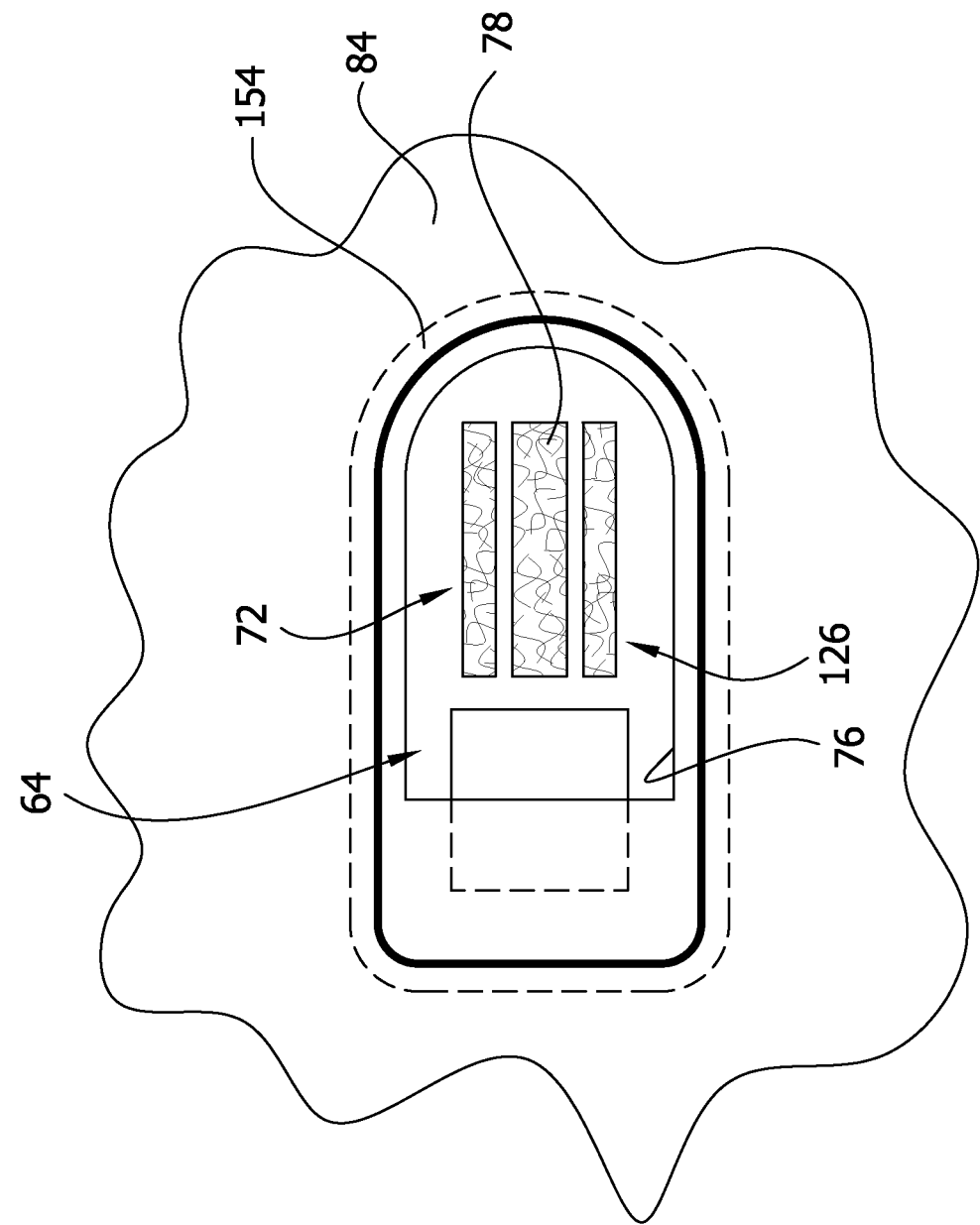
FIG. 10 is an enlarged plan view showing a portion of the bladder and the port secured to the bladder sheet.

As shown in FIGS. 9 and 10, the bladder opening 76 may be sized larger than the port outlet 72 so the bladder opening does not restrict flow of air from the port outlet into the inflatable chamber 74. In the illustrated embodiment, the bladder opening 76 has a keyhole shape (e.g., approximately 0.40 in. (1.02 cm) wide and 0.70 in. (1.78 cm) long). An example weld line for securing the port 64 to the outer bladder sheet 84 is indicated at 154. Bladder openings with different shapes and larger or smaller sizes are within the scope of the present invention.

Figure 11:
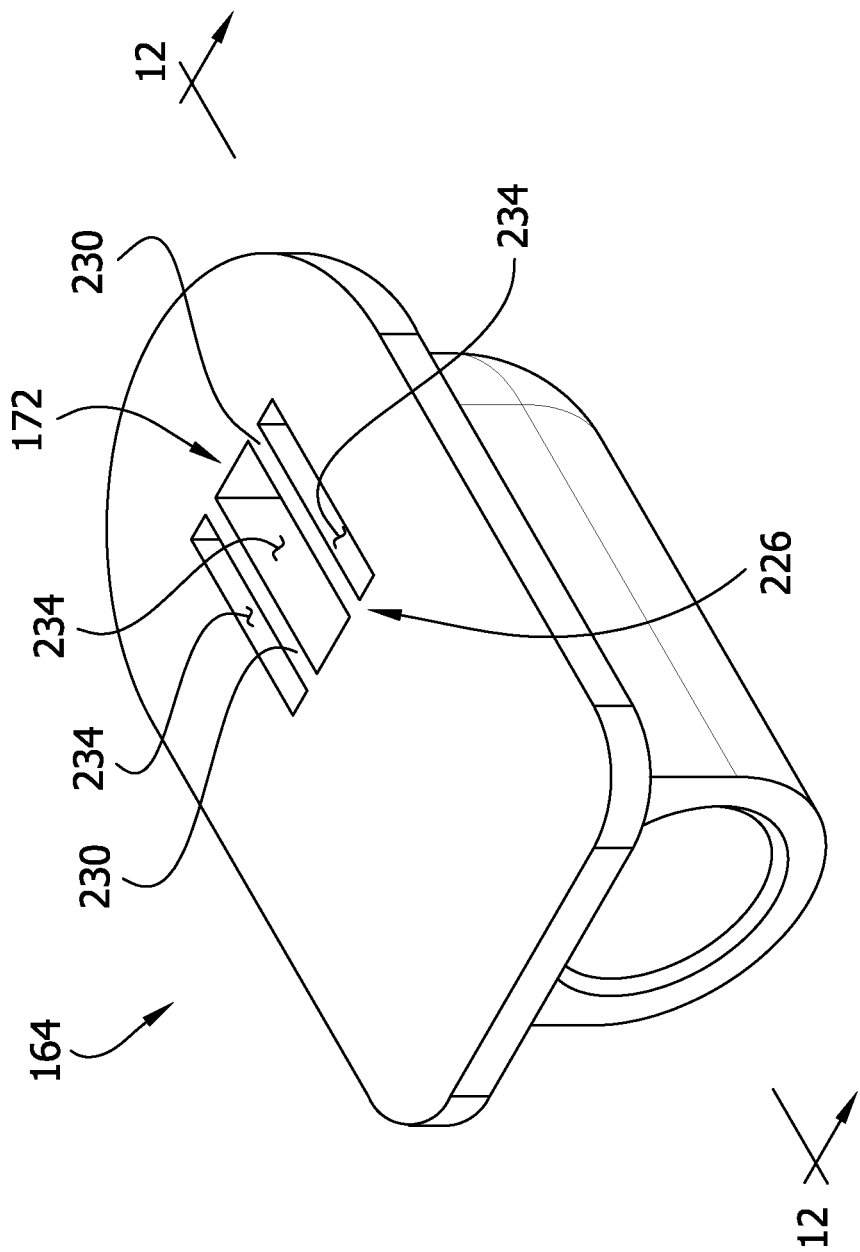
FIG. 11 is an enlarged top perspective of a port of the bladder assembly.
Figure 12:
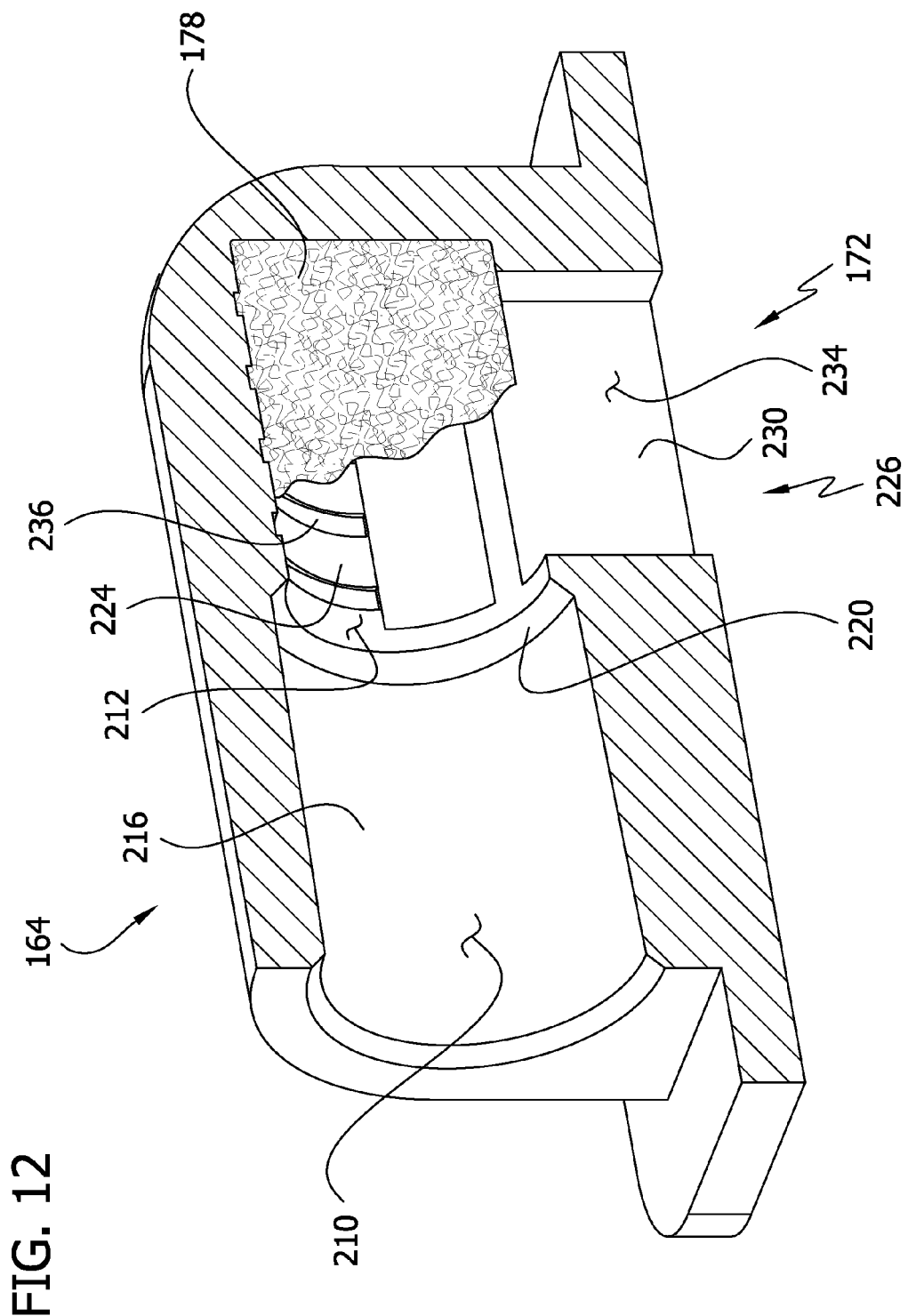
FIG. 12 is an enlarged section of the port of FIG. 11 taken in the plane including line 12-12 in FIG. 11.

FIGS. 11 and 12 show a second embodiment of a port 164 according to the present invention. The port 164 is similar to the port 64 and corresponding parts are indicated by similar reference numbers plus 100. The port 164 is similar in that it has first and second chambers 210 and 212 and a circumferential shoulder 220 extending radially inward from a sidewall 216 of the first chamber 210. In addition, the port 164 has a retainer 226 comprising ribs 230 extending across the air outlet 172 longitudinally of the port that divide the air outlet into three separate rectangular openings 234. The port 164 is different in that it has a shorter overall length (e.g., approximately 1.13 in. (2.87 cm)). Accordingly, the rectangular openings 234 are shorter in length and result in a port outlet 172 with a smaller flow area (e.g., approximately 0.07 in$^2$ (0.45 cm$^2$)). The retainer 226 may further comprise grooves 236 cut into an interior surface of the port 164 such as the side wall 224 of the second chamber 212. The grooves 236 receive portions of the porous insert 178 so that the porous insert resists movement in the direction of fluid flow when fluid is delivered through the port 164.

Figure 13:
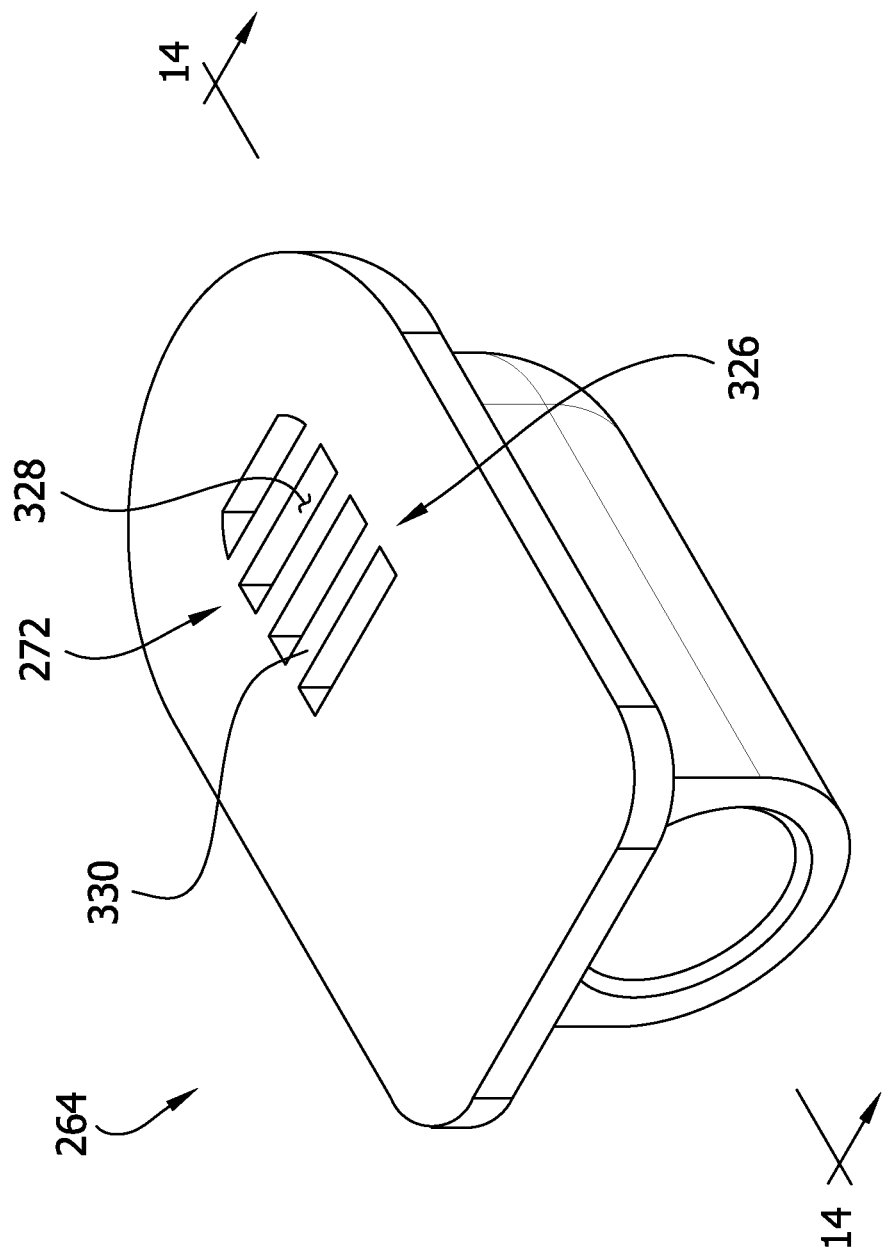
FIG. 13 is an enlarged top perspective of a port of the bladder assembly.
Figure 14:
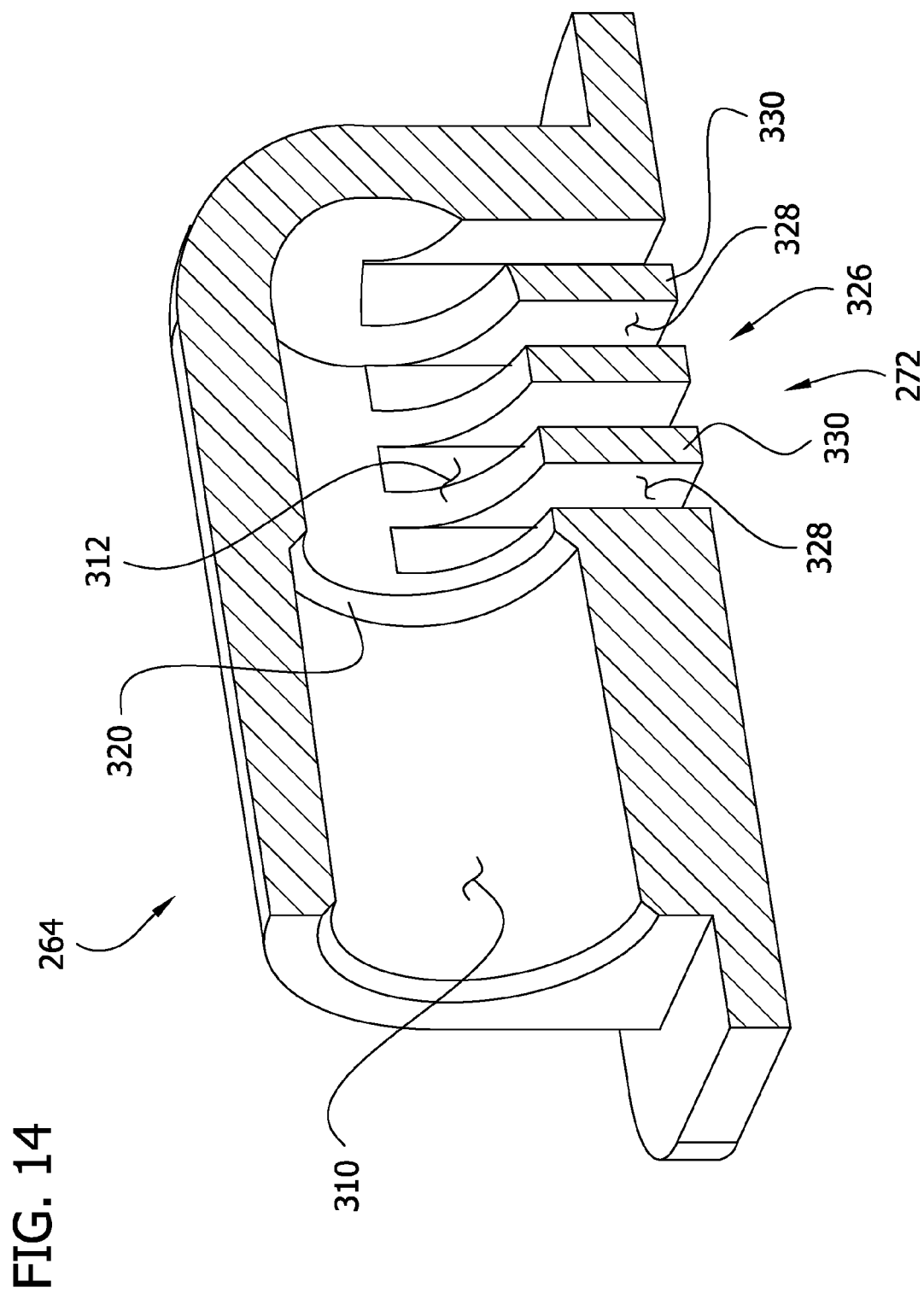
FIG. 14 is an enlarged section of the port of FIG. 13 taken in the plane including line 14-14 in FIG. 13.

FIGS. 13 and 14 show a third embodiment of a port 264 according to the present invention. The port 264 is similar to the first port 64 and corresponding parts are indicated by similar reference numbers plus 200. The port 264 has first and second chambers 310 and 312 and a circumferential shoulder 320. This port 264 is different from those described above in that the port has a retainer 326 comprising three ribs 330 that extend across the air outlet 272 transversely of the port. The ribs 330 divide the air outlet 272 into four separate openings 328. The port 264 is sized approximately the same as the port 164.

Figure 15:
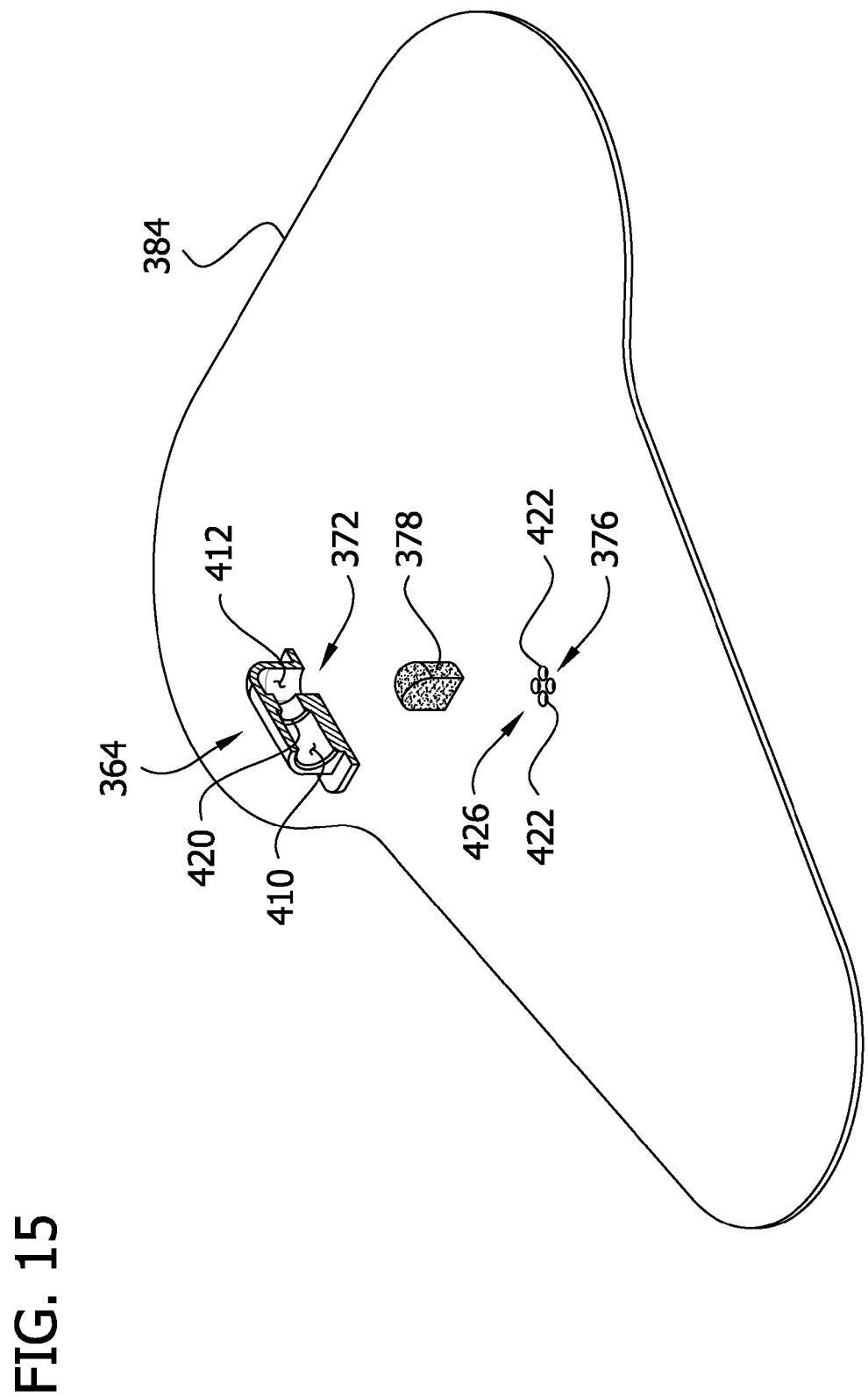
FIG. 15 is an exploded perspective of a port, porous insert and bladder sheet of the bladder assembly.

FIG. 15 shows another embodiment of a port 364, porous insert 378 and outer bladder sheet 384. This embodiment is similar to the first embodiment, and corresponding parts are indicated by similar reference numbers plus 300. The port 364 is similar to the port 64 in that it has first and second chambers 410 and 412 a circumferential shoulder 420. However, in this embodiment, the port 364 does not have ribs for holding the porous insert 378 within the port. Instead, the port 364 has a retainer 426 comprising an edge margin of the outer bladder sheet 384 around the bladder opening 376. In this embodiment, the bladder opening 376 comprises four circular openings 422, and the porous insert 378 is held within the port 364 by edge margins of the outer bladder sheet 384 around the four openings. The bladder opening 376 may comprise more or fewer openings 422 and have shapes other than circular. In manufacture, the porous insert 378 is installed in the port 364 through the port outlet 372. The port 364 is then secured to the outer bladder sheet 384. The porous insert 378 is sized sufficiently large so that it resists movement into the first chamber 410 of the port 364. The illustrated porous insert 378 is shaped to correspond to inside surfaces of the port 364 and the outer bladder sheet 384.

In use, the foot cuff 10 is fluidly connected to a vascular compression inflation controller (not shown). Compressed air is delivered to the bladder 56 of the foot cuff 10 via the port 64 and bladder opening 76 to apply compressive pressure to a foot of a wearer. The porous insert 78 reduces noise generated during inflation of the inflatable chamber 74 of the bladder 56. The ports 164, 264 and 364 are used in a similar fashion.

Testing has demonstrated that compression garments constructed according to the principles of the present invention perform as well as standard or conventional compression garments and generate significantly less noise during inflation. FIG. 16 is a table showing test results comparing performance criteria of a standard compression garment and compression garments having ports constructed according to embodiments described above. Two sets of testing were conducted using two different vascular compression inflation controllers. In each set of testing, performance criteria of a standard port (having no porous insert) was compared to performance criteria of compression garments having ports with porous inserts according to the present invention. In the table of FIG. 16, E1 refers to a port constructed according to the first embodiment described above (port 64), and E2 refers to a port constructed according to the second embodiment described above (port 164). Each type of port was tested with porous inserts of open cell polyurethane foam having uncompressed porosities of 10 ppi (25.4 ppc) and 20 ppi (50.8 ppc).

The performance criteria evaluated in the testing included peak flow rate, rise time to peak pressure, and maximum noise generated during inflation. FIG. 17 is an example graph of data collected during an inflation cycle of a compression garment during testing. The graph illustrates how values for such performance criteria were determined. Peak flow rate refers to the peak air flow measured inline with the air delivery tube near the port of a compression garment. Peak pressure refers to the maximum pressure inside the bladder. Rise time to peak pressure refers to time taken to reach peak pressure from baseline pressure before the bladder is inflated.

Referring again to FIG. 16, the first and second sets of test results demonstrate that compression garments constructed according to the principles of the present invention produce significantly less noise yet have minimal or no impact on peak flow rate and rise time to peak pressure compared to compression garments having standard ports without porous inserts. According to the first set of test results, the compression garments having ports with porous inserts accomplished reduction of peak noise ranging between approximately 11.6 to 12.3 decibels. This reduction of peak noise was realized without adversely impacting peak flow rate or rise time to peak pressure. The mean peak flow rate for the standard port was approximately 72.1 liters per minute (LPM), and the mean peak flow rate for the ports with porous inserts ranged between approximately 70 and 74 LPM. The mean rise time to peak pressure for the standard port was approximately 0.14 seconds, and the mean peak flow rate for the ports with porous inserts ranged between approximately 0.14 and 0.15 seconds. According to the second set of test results, the compression garments having ports with porous inserts accomplished reduction of peak noise ranging between approximately 9.1 to 12.1 decibels. The mean peak flow rate for the standard port was approximately 69.7 LPM, and the mean peak flow rate for the ports with porous inserts ranged between approximately 67.6 and 70.8 LPM. Finally, the mean rise time to peak pressure for the standard port was approximately 0.14 seconds, and the mean peak flow rate for the ports with porous inserts ranged between approximately 0.14 and 0.15 seconds. Therefore, compression garments constructed according to the principles of the present invention produce significantly less noise without adversely impacting performance of the compression garment.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A reduced noise pneumatic compression garment comprising:
    a flexible member adapted to conform to at least a portion of a limb of a human body and to retain itself on the limb;
    a bladder associated with the flexible member conformable to at least a portion of the limb, the bladder defining an inflatable chamber and having an opening through which the inflatable chamber is inflated;
    a port mounted on the bladder, the port having an air inlet, an air outlet, and an air flow path between the air inlet and air outlet, wherein the air inlet is adapted for communication with a source of pressurized air and the air outlet is in communication with the inflatable chamber via the opening in the bladder for delivery of air from the source of pressurized air into the inflatable chamber through the air flow path for inflating the inflatable chamber and thereby applying a compression force to the limb when the flexible member is on the limb; and
    a porous insert located within the flow path of the port between the air inlet and the air outlet for reducing noise from air flow through the port into the inflatable chamber.

2. A compression garment as set forth in claim 1, wherein the porous insert defines a multiplicity of labyrinthine internal passages arranged to provide fluid communication through the porous insert to make flow of air delivered into the inflatable chamber through the port more laminar.

3. A compression garment as set forth in claim 1, wherein the porous insert is open cell foam.

4. A compression garment as set forth in claim 1, wherein the porous insert is made of a compressible material and is disposed within the port in a compressed state.

5. A compression garment as set forth in claim 4, wherein the porous insert has an uncompressed porosity between 100 ppi and 5 ppi (254 ppc and 12.7 ppc).

6. A compression garment as set forth in claim 5, wherein the porous insert has an uncompressed porosity between 60 ppi and 5 ppi (152.4 ppc and 12.7 ppc).

7. A compression garment as set forth in claim 6, wherein the porous insert has a porosity between 40 ppi and 10 ppi (101.6 ppc and 25.4 ppc).

8. A compression garment as set forth in claim 7, wherein the porous insert is open cell foam.

9. A compression garment as set forth in claim 1, wherein the porous insert is disposed within the port in an uncompressed state.

10. A compression garment as set forth in claim 9, wherein the porous insert is a rigid plastic-based matrix.

11. A compression garment as set forth in claim 1, wherein the porous insert has a pore size between 500 μM and 125 μM.

12. A compression garment as set forth in claim 1, further comprising a retainer for retaining said porous insert within the port when air is delivered through the port into the inflatable chamber.

13. A compression garment as set forth in claim 12, wherein the retainer comprises at least one rib extending into at least a portion of said air flow path of the port.

14. A compression garment as set forth in claim 13, wherein the rib extends across the air outlet of the port.

15. A compression garment as set forth in claim 13, wherein the rib is formed as one piece with the port.

16. A compression garment as set forth in claim 12, wherein the retainer comprises at least one groove on an interior surface of the port, wherein the groove receives a portion of the porous insert so that the porous insert resists movement in the direction of fluid flow when fluid is delivered through the port.

17. A compression garment as set forth in claim 12, wherein the retainer comprises an adhesive between an interior surface of the port and the porous insert.

18. A compression garment as set forth in claim 12, wherein the port is affixed to a sidewall of the bladder such that the air outlet of the port overlies the opening in the bladder, the opening in the bladder being sized smaller than the porous insert, and the retainer comprises at least a portion of an edge margin of the bladder sidewall around the opening.

19. A compression garment as set forth in claim 17, wherein the opening in the bladder comprises more than one opening and the retainer comprises at least a portion of an edge margin of the bladder sidewall around at least one of the openings.

20. A method of quietly inflating a pneumatic compression garment, the method comprising:
    delivering a flow of pressurized gas through a port to an inflatable chamber of a flexible member adapted to be received on a human body to compress the body;
    changing a direction of flow of the pressurized gas between an inlet of the port and an outlet of the port;
    diffusing the flow of pressurized gas to the inflatable chamber through labyrinthine passages within the port; and
    passing the diffused flow into the inflatable chamber.

* * * * *